United States Patent [19]

Alexander et al.

[11] Patent Number: 5,453,558
[45] Date of Patent: Sep. 26, 1995

[54] DEHYDROGENATION CATALYST AND PROCESS

[75] Inventors: Bruce D. Alexander, Villa Park; George A. Huff, Jr., Naperville, both of Ill.

[73] Assignee: Amoco Corporation, Chicago, Ill.

[21] Appl. No.: 270,443

[22] Filed: Jul. 5, 1994

[51] Int. Cl.$^6$ ............................ C07C 5/333; C10G 35/09
[52] U.S. Cl. ............................................ 585/660; 208/138
[58] Field of Search ............................ 208/133, 138, 208/141; 585/654, 660, 661

[56] References Cited

U.S. PATENT DOCUMENTS 4,619,906 10/1986 Lambert et al. ............................ 502/66
4,652,689 3/1987 Lambert et al. ............................ 585/415
4,727,216 2/1988 Miller ............................ 585/660

*Primary Examiner*—Asok Pal
*Assistant Examiner*—Bekir L. Yildirim
*Attorney, Agent, or Firm*—Thomas A. Yassen; Richard A. Kretchmer

[57] ABSTRACT

A process and catalyst are provided for dehydrogenating a hydrocarbon feedstock and producing an olefinic product. The process comprises contacting the feedstock at dehydrogenation conditions with a dehydrogenation catalyst comprising from about 0.01 weight percent to about 5.0 weight percent of a platinum group metal, from about 0.02 weight percent to about 10.0 weight percent of zinc, and a support component comprising L zeolite and an alkali metal.

13 Claims, No Drawings

DEHYDROGENATION CATALYST AND PROCESS

BACKGROUND OF THE INVENTION

This invention relates to a process and catalyst for the dehydrogenation of hydrocarbons. More particularly, this invention relates to a catalyst and process for the dehydrogenation of paraffinic hydrocarbon utilizing a catalyst comprising a platinum group metal and zinc on a support component comprising L-zeolite and an alkali metal, useful for the production of high oxygen-content fuels blending components (Oxygenates) and chemical industry feedstocks.

Oxygenates have been part of the United States gasoline strategy since the late 1970s. With the recent enactment of the Clean Air Act Amendments of 1990, the demand for oxygenates has increased again such that gasoline is now being blended to 2.7 weight percent oxygen and is being marketed in numerous metropolitan areas that have failed to meet carbon monoxide pollution standards. In the near future, it is expected that between 30 and 60 percent of the United States gasoline pool may require oxygenates.

The most commonly used oxygenates today are methanol, ethanol, and ethers such as methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. As a result of the above, MTBE has become particularly attractive.

Homologues of MTBE such as ethyl tertiary butyl ether (ETBE) and methyl tertiary amyl ether (TAME) are also gaining industry acceptance. Moreover, commercial activity with respect to ETBE and TAME is expected to increase relative to MTBE, in view of recent Environmental Protection Agency decisions to reduce the RVP requirements for gasolines well below 9 psia, the blending RVP of MTBE.

Ether production capacity, however, is often limited by iso-olefin feedstock availability. Commercial MTBE and ETBE processes both utilize isobutylene as a feedstock while TAME processes utilize isoamylene as a feedstock. Isobutylene and isoamylene are generally supplied to a commercial ether process from a fluid catalytic cracking unit (FCC), a fluidized or delayed coker, or from downstream paraffin isomerization and dehydrogenation facilities, As a result, the availability of hydrocarbons having 4 or 5 carbon atoms is limited by constraints such as, but not limited to, crude properties, FCC catalyst properties and operating conditions, coking conditions, as well as by other refinery operating constraints. The chemical mix of $C_4$ and $C_5$ paraffins, olefins, and aromatics as well as the particular mix of iso-olefins to normal olefins are similarly constrained.

The relatively high ratio of capital and operating costs to the throughput of ether product subsequently produced from the construction of new facilities for increasing ether process feedstocks further exacerbates oxygenate supply. These costs are generally attributed to the high degree of complexity and the sophisticated equipment connected to the operation of dehydrogenation or isomedzation processes such as, but not limited to, desulfurization, catalytic reactor, and hydrogen supply and recirculation systems. The profitability of such new facilities is often dependent on the ability of the refiner to keep construction costs low and operating throughput high.

Thus, there exists a great need in the petroleum industry for a low cost method of increasing oxygenate production feedstocks that overcomes or avoids the obstacles described above and that is economically viable in terms of construction cost and facility utilization.

Processes for dehydrogenating paraffins in the presence of hydrogen and a catalyst comprising a platinum group metal on an amorphous alumina support have been disclosed in the art.

For example, U.S. Pat. Nos. 4,190,521, 4,374,046, and 4,458,098 to Antos disclose a catalyst comprising a platinum group component, nickel, and a zinc on a porous carrier material such as alumina for dehydrogenating paraffinic hydrocarbon.

U.S. Pat. No. 4,438,288 to Imai et al. discloses a dehydrogenation process using a catalyst comprising a platinum group component, an alkali or alkaline earth component, and optionally a Group IV component such as tin, on a porous support material such as alumina. The properties and characteristics of the catalyst generally necessitate periodic catalyst regeneration in the presence of a halogen.

Processes for dehydrogenating paraffins in the presence of hydrogen and a catalyst comprising a platinum group metal on a silicalite molecular sieve support have also been disclosed in the art.

For example, U.S. Pat. Nos. 4,665,267 and 4,795,732 to Barri and U.S. Pat. Nos. 5,208,201, and 5,126,502 to Barri et al. disclose processes for dehydrogenation of $C_2$ to $C_{10}$ paraffins using a catalyst comprising zinc and a platinum group metal on a support having the silicalite structure wherein the framework of the structure consists essentially of silicon and oxygen atoms or of silicon, zinc, and oxygen atoms. The catalyst is generally formed such that it is substantially free of all alkali or alkaline earth metals.

A process for dehydrogenating paraffins in the presence of a catalyst comprising a platinum group metal on an L zeolite molecular sieve support has also been disclosed in the art.

U.S. Pat. No. 4,727,216 to Miller discloses a process for dehydrogenating isobutane in the presence of a sulfur-containing gas and a dehydrogenation catalyst. The dehydrogenation catalyst comprises a sulfided L zeolite containing from 8–10% by weight barium, from 0.6–1.0% platinum, and tin at an atomic ratio with the platinum of about 1:1. The dehydrogenation catalyst further comprises an inorganic binder selected from the group consisting of silica, alumina, and aluminosilicates.

While the above-described processes and catalysts have achieved varying degrees of laboratory success, it has been found that in commercial application, catalysts such as those described above have been prone to early deactivation and short on-stream run lengths. In order to overcome this obstacle, the process operator has generally needed to perform the dehydrogenation reaction in the presence of supplemental hydrogen for reducing catalyst coke formation. Supplemental hydrogen supply facilities are particularly complex and generally require costly compression and hydrogen purification equipment. Moreover, supplemental hydrogen addition drives the dehydrogenation reaction stoichiometrically away from dehydrogenation and towards olefin saturation.

Notwithstanding the presence of supplemental hydrogen addition and recirculation equipment, the process operator has still generally needed to resort to catalyst regeneration. Catalyst regeneration is generally performed in large, high temperature catalyst regenerators present in fluidized bed/ riser schemes or through periodic and frequent batch regeneration such as performed with semi-regenerative fixed bed schemes. Catalyst regeneration facilities are extremely costly. For fixed bed reaction schemes, an additional swing reactor must be erected and the process operated with at least one reactor off-stream and in regeneration mode all of the time.

It has now been found that a dehydrogenation catalyst comprising a platinum group metal and zinc on a support comprising L zeolite and an alkali metal provides superior dehydrogenation performance in terms of paraffin conversion, olefin selectivity, and olefin yield to that of the prior art dehydrogenation catalysts and maintains such level of superior performance, without regeneration, far longer than any of the prior art catalysts tested to date.

It has also been found that a dehydrogenation catalyst comprising a platinum group metal and zinc on a support comprising L zeolite and an alkali metal provides such an extended operating cycle life, that it can be used with or without supplemental hydrogen addition while still achieving superior levels of performance.

For purposes of the present invention, paraffin conversion, olefin selectivity, and olefin yield shall have the following meanings and shall be calculated by mole and in accordance with the following models:

Paraffin Conversion =

$$\frac{100 - \text{Mol}\%\text{H}_{2\,product} - \text{MOl}\%\text{Paraffin}_{product}}{100 - \text{Mol}\%\text{H}_{2\,product}} \times 100$$

Olefin Selectivity =

$$\frac{\text{Mol}\%\text{Olefin}_{product}}{100 - \text{Mol}\%\text{H}_{2\,product} - \text{Mol}\%\text{Paraffin}_{product}} \times 100$$

Olefin Yield =

$$\frac{(\text{Olefin Selectivity}) \times (\text{Paraffin Conversion})}{100}$$

It is therefore an object of the present invention to provide a dehydrogenation process and catalyst that effectively dehydrogenate paraffinic hydrocarbon.

It is another object of the present invention to provide a dehydrogenation catalyst that resists deactivation and prolongs catalyst cycle life under dehydrogenation conditions.

It is yet another object of the present invention to provide a dehydrogenation process and catalyst that can be effectively operated in the absence of supplemental hydrogen addition.

It is still another object of the present invention to provide a dehydrogenation process that, in view of its simplicity, can be adapted to utilize equipment from any of several existing petroleum refinery or chemical plant operating facilities.

Other objects appear herein.

SUMMARY OF THE INVENTION

The above objects can be achieved by providing a process for dehydrogenating a hydrocarbon feedstock and producing an olefinic product comprising contacting the feedstock at dehydrogenation conditions with a dehydrogenation catalyst comprising from about 0.01 weight percent to about 5.0 weight percent of a platinum group metal, from about 0.02 weight percent to about 10.0 weight percent of zinc, and a support component comprising L zeolite and an alkali metal.

In another embodiment, the above objects can be achieved by providing a dehydrogenation catalyst comprising from about 0.01 weight percent to about 5.0 weight percent of a platinum group metal, from about 0.02 weight percent to about 10.0 weight percent of zinc, an L zeolite molecular sieve, and from about 0.10 weight percent to about 10.0 weight percent of an alkali metal.

The dehydrogenation catalyst and process of the present invention provide superior overall dehydrogenation properties and particularly extraordinary levels of paraffin conversion closely approaching thermodynamic equilibrium. The paraffin conversion and olefin selectivity attendant to the dehydrogenation catalyst and process of the present invention generally result in olefin yield levels in excess of 25 percent, typically in excess of 30 percent, and commonly in excess of 35 percent.

The dehydrogenation catalyst and process of the present invention provide the above-described levels of performance while resisting deactivation under dehydrogenation conditions, thereby extending catalyst cycle life. The dehydrogenation catalyst of the present invention can and has achieved olefin yield deactivation loss levels as low as 0.4 percent conversion per day or less at a reaction temperature of 1000° F. The dehydrogenation catalyst and process of the present invention can be utilized for on stream periods in excess of 140 hours at a reaction temperature of 1000° F. before requiring catalyst regeneration or replacement.

The dehydrogenation catalyst and process of the present invention are so effective with regard to catalyst stability and deactivation resistance that the catalyst can be operated in the absence of supplemental hydrogen addition. Operating in the absence of supplemental hydrogen addition not only avoids the enormous capital and operating costs connected to the installation and operation of hydrogen recovery facilities but also favorably drives the dehydrogenation reaction stoichiometrically towards increased dehydrogenation and olefin yield and away from olefin saturation.

The dehydrogenation catalyst and process of the present invention can be retrofitted to utilize existing processes and facilities such as, but not limited to those formerly dedicated to naphtha reforming. A catalytic reformer can possess reaction systems and manifolding, furnace hardware, hydrocarbon separation, and catalyst regeneration equipment particularly synergistic to use with the process of the present invention.

BRIEF DESCRIPTION OF THE INVENTION

The hydrocarbon feedstock suitable for use with the present invention generally comprises paraffinic hydrocarbons having from about 2 to 20 carbon atoms and more preferably from about 2 to 12 carbon atoms for best results. The preferred hydrocarbon feedstock boils at a temperature of below 700° F. at atmospheric pressure and more preferably below 450° F. at atmospheric pressure.

In one embodiment, the process can be provided for dehydrogenating hydrocarbon for direct or eventual upgrade to ethers such as, but not limited to, MTBE, ETBE, and TAME. Feedstocks for use with the present invention and suitable for providing etherification feedstocks will generally comprise aliphatic or alicyclic hydrocarbon having from 3 to 7 carbon atoms. The preferred feedstocks generally comprise at least 5 weight percent paraffinic hydrocarbon and more preferably at least 10 weight percent paraffinic hydrocarbon to justify the capital and operating costs to perform dehydrogenation. Since most etherification processes convert iso-olefins to ethers, the feedstock to such processes often requires isomerization prior to etherification. The feedstock suitable for use with the present invention can effectively dehydrogenate isoparaffins as well as normal paraffins therefore providing the flexibility to incorporate the process upstream, downstream or concurrent with an isomerization step.

In a second embodiment, the process can be provided for dehydrogenating hydrocarbon for improving gasoline research and/or motor octane. Generally, olefinic hydrocarbon boiling in the gasoline or naphtha boiling point temperature range has a higher research and motor octane than its paraffinic counterparts. At least a portion of such feedstocks will generally comprise paraffinic hydrocarbon having from 4 to 12 carbon atoms and the paraffinic hydrocarbon can be normal, isomeric, or a combination thereof.

In a third embodiment, the process can be provided to dehydrogenate hydrocarbon for feed to a petroleum refinery alkylation process. Feedstocks suitable for dehydrogenation in accordance with the present invention and for providing alkylation unit feedstock preferably comprise paraffinic hydrocarbon having from 3 to 6 carbon atoms and more preferably from 3 to 5 carbon atoms. The paraffinic fraction of the feedstock can be normal, isomeric, or a combination thereof.

In still another embodiment, the process can be provided to dehydrogenate hydrocarbon as feed for commercial chemical manufacture. Feedstocks having from 2 to 4 carbon atoms can be dehydrogenated into olefinic feedstocks for the subsequent production of polyethylene, polypropylene, polybutene, or other chemical compositions that are commonly sold in solid or liquid forms.

The above feedstocks can be processed through the process of the present invention neat or can be combined with recycled portions of the product stream from the dehydrogenation process. Similarly, combinations of the above-described feedstock embodiments can be directed to the process of the present invention and the products subsequently fractionated to individual product pools. The process of the present invention can also be operated in "blocked out" mode where only one feedstock is processed through the facility at any one time. Blocked out operation simplifies processing capital requirements but can also increase tankage capital and inventory holding costs. Other feedstock combinations and methods to comport the process of the present invention to individual needs will be known to those skilled in the art.

The process of the present invention comprises a dehydrogenation catalyst comprising a platinum group metal and zinc on a support component comprising an L zeolite molecular sieve and an alkali metal. The L zeolite molecular sieve-containing support can also comprise an inorganic oxide binder.

The composition of L zeolite may be stoichiometrically expressed in terms of moles of oxides as follows:

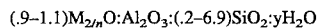

where M designates at least one exchangeable cation, as hereinbelow defined, n represents the valence of M, and y may be any value of from 0 to about 9.

Minor variations in the mole ratios of the oxides within the ranges indicated by the above formula do not significantly change the crystal structure or physical properties of the zeolite. Likewise, the value of y is not necessarily an invariant for all samples of L zeolite. This is true because the various exchangeable cations are of different size, and as no appreciable modification of the crystal lattice dimensions of the zeolite is effected by the exchange of these particular cations, more or less interstitial space should be available for the accommodation of water molecules. Therefore, the value of y depends upon the identity of the exchangeable cation and also upon the degree of dehydration of the zeolite.

The exchangeable cations contemplated by the present invention include mono-, di-, and trivalent metal ions, particularly those of Groups I, II, and III of the Periodic Table (IUPAC) such as barium, calcium, cerium, lithium, magnesium, potassium, sodium, strontium. zinc ions, and the like, and other cations such as hydrogen and ammonium ions, which with L zeolite, behave like the metal ions mentioned above in that they may be replaced for other exchangeable cations without causing a substantial alteration of the basic crystal structure of the zeolite. Of the exchangeable cations, mono- and divalent cations are especially satisfactory in the invention since they are generally more easily included within the cavities of the zeolite crystal.

Although there are a number of cations that may be present in L zeolite, it is preferred to synthesize the potassium form of the zeolite, i.e. the form in which the exchangeable cations present are substantially all potassium cations. The reactants accordingly employed are readily available and generally water soluble. The exchangeable cations present in the zeolite may then conveniently be replaced by other exchangeable cations, as will be shown below, thereby yielding an isomorphic form of L zeolite.

In one method of making L zeolite, the potassium form of L zeolite is prepared by suitably heating an aqueous metal aluminosilicate mixture whose composition, expressed in terms of the mole ratios of oxides, falls within the ranges of:

| | |
|---|---|
| $K_2O/(K_2O + Na_2O)$ | From about 0.33 to about 1 |
| $(K_2O + Na_2O)/SiO_2$ | From about 0.35 to about 0.5 |
| $SiO_2/Al_2O_3$ | From about 10 to about 28 |
| $H_2O/(K_2O + Na_2O)$ | From about 15 to about 41 |

The desired product is thereby crystallized out relatively free from zeolites of dissimilar crystal structure.

The potassium form of L zeolite may also be prepared using another method, along with other zeolitic compounds, by employing a reaction mixture whose composition, expressed in terms of mole ratios of oxides, falls within the following ranges of:

| | |
|---|---|
| $K_2O/(K_2O + Na_2O)$ | From about 0.26 to about 1 |
| $(K_2O + Na_2O)/SiO_2$ | From about 0.34 to about 0.5 |
| $SiO_2/Al_2O_3$ | From about 15 to about 28 |
| $H_2O/(K_2O + Na_2O)$ | From about 15 to about 51 |

It is noted that the presence of sodium in the reaction mixture is not critical to the present invention.

When the zeolite is prepared from the reaction mixtures containing sodium, sodium ions are generally also included within the product as part of the exchangeable cations together with the potassium ions. The product obtained from the above ranges has a composition, expressed in terms of moles of oxides, corresponding to the formula:

where x may be any value of from 0 to about 0.75 and y may be any value of from 0 to about 9.

L zeolite has been characterized in "Zeolite Molecular Sieves" by Donald W. Breck, John Wiley & Sons, 1974, as having a framework comprising 18 tetrahedra unit cancrinite-type cages linked by double 6-rings in columns crosslinked by single oxygen bridges to form planar 12-membered rings. These 12-membered rings produce wide channels parallel to the c-axis with no stacking faults. Unlike erionite and cancrinite, the cancrinite cages are symmetrically placed across the double 6-ring units. There are four types of cation locations: A in the double 6-rings; B in the cancrinite-type cages; C between the cancrinite-type cages; and D on the channel wall. The cations in site D appear to be the only exchangeable cations at room temperature. During dehydration, cations in site D probably withdraw from the channel walls to a fifth site, site E, which is located between the A sites. The hydrocarbon sorption pores are approximately 7 to 8 Angstroms in diameter.

A more complete description of L zeolite is given in U.S. Pat. No. 3,216,789 which is hereby incorporated by reference.

L zeolite is a large pore zeolite (i.e., having a pore size of at least 6 Angstroms). Other large pore zeolites include A, X, Y, omega, and mordenite. L zeolite differs from these other large pore zeolites in a variety of ways, besides X-ray diffraction pattern.

One of the most pronounced differences is in the channel system of L zeolite. L zeolite has a one-dimensional channel system parallel to the c-axis, while most other zeolites have either two-dimensional or three dimensional channel systems. Zeolites A, X, and Y all have three-dimensional channel systems. Mordenite has a major channel system parallel to the c-axis, and another very restricted channel system parallel to the b-axis. Omega zeolite has a one-dimensional channel system.

Another pronounced difference is in the framework of the various zeolites. Only L zeolite has cancrinite-type cages linked by double-six rings in columns and crosslinked by oxygen bridges to form planar 12-rings. Zeolite A has a cubic array of truncated octahedra, beta cages linked by double-four ring units. Zeolites X and Y both have truncated octahedra, beta cages linked tetrahedrally through double-six rings in an arrangement like carbon atoms in a diamond. Mordenite has complex chains of five-rings crosslinked by four-ring chains. Omega has a fourteen-hedron of gmelinite-type linked by oxygen bridges in columns parallel to the c-axis.

Presently, it is not known which of these differences, or other differences, is responsible for the high paraffin dehydrogenation selectivity of the catalyst of the present invention comprising L zeolite, but it is known that the catalyst of the present invention comprising L zeolite does react differently than catalysts made of other zeolites.

Various factors have an effect on the X-ray diffraction pattern of a generic zeolite. Such factors include temperature, pressure, crystal size, impurities, and the type of cations present. For instance, as the crystal size of the L zeolite becomes smaller, the X-ray diffraction pattern becomes broader and less precise. Thus, the term "L zeolite" includes any zeolites made up of cancrinite cages having an X-ray diffraction pattern substantially similar to the X-ray diffraction patterns shown in U.S. Pat. No. 3,216,789.

Crystal size also has an effect on the stability of the catalyst. For reasons not yet fully understood, catalysts having at least 80% of the L zeolite crystals of a size larger than 1000 Angstroms generally result in longer run lengths than catalysts having substantially all of the L zeolite crystals at a size of between 200 and 500 Angstroms. Thus, larger L zeolite crystallite sizes are generally preferred.

In making L zeolite, representative reactants are activated alumina, gamma alumina, alumina trihydrate, and sodium alumina as a source of alumina. Silica may be obtained from sodium or potassium silicate, silica gels, silicic acid, aqueous colloidal sols, and reactive amorphous solid silicas. The preparation of typical silica sols which are suitable for use in the catalyst of the present invention are described in U.S. Pat. No. 2,574,902 and U.S. Pat. No. 2,597,872 which are hereby incorporated by reference. Typical of the group of reactive amorphous solid silicas, preferably having an ultimate particle size of less than 1 micron, are such materials as fume silicas, chemically precipitated and precipitated silica sols, and silicas such as that known by the trade name of "CAB-O-SIL EH-5" and manufactured by Cabot Corporation. Potassium and sodium hydroxide may supply the metal cation and assist in controlling pH.

A typical method for synthesizing L zeolite comprises dissolving potassium or sodium aluminate and alkali, viz., potassium, or sodium hydroxide, in water. This solution is admixed with a water solution of sodium silicate, or preferably with a water-silicate mixture derived at least in part from an aqueous colloidal silica sol. The resultant reaction mixture is generally placed in a container made, for example, of metal or glass. The container should be closed to prevent loss of water. The reaction mixture is then stirred to insure homogeneity.

The zeolite may be satisfactorily prepared at temperatures of from about 90° C. to about 200° C. and at atmospheric pressure or as high or higher than that pressure corresponding to the vapor pressure of water in equilibrium with the mixture of reactants at the higher temperature. Any suitable heating apparatus, e.g., an oven, sand bath, oil bath or jacketed autoclave, may be used. Heating is generally continued until the desired crystalline zeolite product is formed. The zeolite crystals are filtered off and washed to separate them from the reactant mother liquor. The zeolite crystals should be washed, preferably with distilled water, until the effluent wash water, in equilibrium with the product, has a pH of between about 9 and 12. As the zeolite crystals are washed, the exchangeable cation of the zeolite may be partially removed and is believed to be replaced by hydrogen cations. If the washing is discontinued when the pH of the effluent wash water is between about 10 and 11, the $(K_2O+Na_2O)/Al_2O_3$ molar ratio of the crystalline product will be approximately 1.0. Thereafter, the zeolite crystals may be dried, typically in a vented oven.

Whether ion exchanged with the L zeolite molecular sieve component prior to incorporation of any other component or post incorporated onto the dehydrogenation catalyst after addition of any one or more of the zinc component, platinum group metal component, or the binder or matrix component, the dehydrogenation catalyst support component comprises a particularly targeted alkali metal concentration. The preferred alkali metals are potassium and sodium with potassium being most preferred. The alkali metal concentration of the dehydrogenation catalyst in accordance with the present invention generally ranges from about 0.1 weight percent to about 10.0 weight percent, calculated as a percentage of the dehydrogenation catalyst, preferably from about 0.5 weight percent to about 8.0 weight percent, and more preferably from about 1.0 weight percent to about 4.0 weight percent for best results.

It has been found that a dehydrogenation process using a comparable dehydrogenation catalyst, but with an alkali metal concentration below the ranges set forth above, can result in substantial reductions in olefin selectivity which generally overwhelm small paraffin conversion increases, resulting in lower olefin yields and inferior dehydrogenation performance. Alkali metal concentration above the ranges set forth above, can result in reductions in paraffin conversion that overwhelm diminishing marginal benefits in olefin selectivity, thereby resulting in lower olefin yields and inferior dehydrogenation performance.

Where the alkali metal concentration of the support comprising an L zeolite molecular sieve would result in a dehydrogenation catalyst having an alkali metal concentration above the particularly targeted concentration range described above, the alkali metal is generally removed by replacement of the alkali metal with ammonium ions followed by decomposition of the ammonium form by calcination.

Where the alkali metal concentration of the support comprising an L zeolite molecular sieve is below the particularly targeted alkali metal concentration, the alkali metal is generally back-added to the support by impregnation employing the heat-decomposable salts of the alkali metal or by other methods known to those skilled in the art such as ion-exchange, with impregnation being preferred. Suitable aqueous impregnation solutions can include, but are not limited to sodium nitrate, sodium acetate, potassium nitrate, potassium acetate, and potassium carbonate.

Impregnation, such as with potassium, using potassium nitrate, potassium acetate, or potassium carbonate can begin by precalcining the L zeolite molecular sieve component in preparation for using incipient wetness techniques. Under conventional incipient wetness techniques, a determination is generally made as to the amount of water required to saturate and fill the pores of the support component. A solution is then prepared utilizing the predetermined amount of water and a sufficient amount of the potassium salt to provide a dehydrogenation catalyst having the desired concentration of potassium. The impregnated support component is then separated, drained, and dried in preparation for calcining. Calcination is generally performed at a temperature ranging from about 600° F. to about 1,202° F. (315° C. to about 650° C.), and preferably from about 700° F. to about 1067° F. (371° C. to about 575° C.) for best results.

The dehydrogenation metals in accordance with the present invention generally include a zinc component in combination with one or more platinum group metals.

The zinc component can be present in its elemental form or as its oxide, sulfide, or mixtures thereof. The zinc component is generally present in the dehydrogenation catalyst in an amount ranging from about 0.02 weight percent to about 10.0 weight percent, preferably from about 0.1 weight percent to about 5.0 weight percent, and more preferably from about 1.0 weight percent to about 4.0 weight percent based on the total weight of the dehydrogenation catalyst and calculated as oxide, for best results.

The platinum group metal component can include one or more of the platinum group metals, preferably platinum or palladium, and more preferably platinum for best results. The platinum group metals can be present in the dehydrogenation catalyst in their elemental form or as their oxides, sulfides, or mixtures thereof. The platinum group metals are cumulatively present in an amount ranging from about 0.01 weight percent to about 5.0 weight percent, preferably from about 0.1 weight percent to about 3.0 weight percent, more preferably from about 0.1 weight percent to about 2.0 weight percent, and most preferably from about 0.1 weight percent to about 1.5 weight percent based on the total weight of the catalyst and calculated as oxide, for best results.

Catalyst dehydrogenation metals concentrations outside of the above-described zinc and cumulative platinum group metals ranges are generally less economic. Higher metals concentrations can require more total dehydrogenation metal component due to reduced dispersion and hydrocarbon/catalyst contact. Lower metals concentrations can result in increased support material requirements, catalyst handling, transportation, and capital costs.

The zinc and platinum group dehydrogenation metal components can be deposed or incorporated upon the support component by impregnation employing heat-decomposable salts of the zinc and platinum group metals or through other methods known to those skilled in the art such as ion-exchange, with impregnation methods being preferred. The zinc and platinum group metals can be impregnated onto the support separately, or can be co-impregnated onto the support. Suitable aqueous impregnation solutions include, but are not limited to, zinc nitrate, zinc chloride, chloroplatinic acid, palladium chloride, tetraamine palladium chloride, and tetraamine platinum chloride.

Impregnation using an impregnation solution comprising zinc nitrate and tetraamine platinum chloride can be performed by precalcining the dehydrogenation support component, in the form of a powder, pellets, extrudates, or spheres and determining the amount of water that must be added to wet all of the material. The zinc nitrate and tetraamine platinum chloride are then dissolved in the calculated amount of water, and the solution added to the support in a manner such that the solution completely saturates the support. The zinc nitrate and tetraamine platinum chloride are added in a manner such that the aqueous solution contains the total amount of elemental zinc and platinum to be deposited on the given mass of support. Impregnation can be performed for each metal separately, including an intervening drying step between impregnations, or as a single co-impregnation step. The saturated support is then generally separated, drained, and dried in preparation for calcining. Commercially, draining volumes can be reduced in order to reduce zinc and platinum losses and waste water handling costs by providing less than the full amount of aqueous solution (such as from 90% to 100% by volume of aqueous solution) necessary to saturate all of the support. Calcination generally is performed at a temperature of from about 600° F. to about 1,202° F. (315° C. to about 650° C.), or more preferably from about 700° F. to about 1,067° F. (371 ° C. to about 575° C.) for best results.

It has been found that combining zinc and platinum group metal components in accordance with the present invention provides substantially improved dehydrogenation stability resulting in longer catalyst cycles between regenerations and extended overall catalyst life before replacement. The zinc and platinum group metals can be added to the catalyst of the present invention in zinc to platinum group weight ratios extending from 10:1 to 1:10, preferably from 7:1 to 1:7, and most preferably from 7:1 to 1:1 for best results.

It has also been found that during dehydrogenation operation in accordance with the present invention, post-analysis of the catalyst after significant hours on stream can show significant reductions in zinc concentration on the catalyst to levels as low as 50 percent, 25 percent, and even 15 percent of the level of the originally impregnated catalyst. This is believed to be true due to volatilization of the impregnated zinc component during dehydrogenation operations where operating temperatures can often exceed 1000° F. While the zinc concentrations and therefore the zinc to platinum ratio tend to be reduced with on stream time, the catalyst performance is generally not substantially effected. Zinc volatilization can be managed by post incorporation of zinc after a regeneration cycle or by addition of a Group IVB metal such as zirconium during initial catalyst formulation.

The dehydrogenation catalyst in accordance with the present invention can and generally comprises various binders or matrix materials depending on the intended process use. The base catalyst can be combined with active or inactive materials, synthetic or naturally-occurring zeolites, as well as inorganic or organic materials which would be useful for binding the L zeolite. Well-known materials include silica, silica-alumina, alumina, alumina sols, hydrated aluminas, clays such as bentonite or kaolin, or other binders known in the art.

Silica is the preferred binder for use with the dehydrogenation catalyst of the present invention. Dehydrogenation catalysts in accordance with the present invention and having silica binders are generally preferable to alternative binders in that they do not generally affect overall catalyst acidity in contradistinction to binders such as alumina and other metal oxides commonly used in catalysis.

The L zeolite molecular sieve component is generally present in the dehydrogenation catalyst of the present invention in an amount ranging from about 5.0 weight percent to about 98.0 weight percent, preferably from about 20.0 weight percent to about 80.0 weight percent, and more preferably from about 40.0 weight percent to about 60.0 weight percent for best results. L zeolite molecular sieve component concentrations as a percentage of the dehydrogenation catalyst, in a range of from about 40.0 weight percent to about 60.0 weight percent, are particularly preferred because it has been found that these levels can promote an optimum balance of paraffin conversion and olefin selectivity for producing maximum volume yields of the desired olefins. Higher percentages of the L zeolite molecular sieve component can result in a softer and less attrition resistant dehydrogenation catalyst which can reduce catalyst life and increase catalyst costs. Lower percentages of the L zeolite molecular sieve component can result in larger catalytic reactor size requirements.

Methods for dispersing the base catalyst comprising the L zeolite molecular sieve and dehydrogenation metal components in accordance with the present invention within a refractory inorganic oxide matrix component are generally well-known to persons skilled in the art. A preferred method is to blend the base catalyst component, preferably in a finely divided form, into a sol, hydrosol, or hydrogel of an inorganic oxide, and then add a gelling medium such as ammonium hydroxide to the blend with stirring to produce a gel. The resulting gel can be dried, dimensionally formed if desired, and calcined. Drying is preferably conducted in air at a temperature of about 80° F. to about 350° F. (about 27° C. to about 177° C.) for a period of several seconds to several hours. Calcination is preferably conducted by heating in air at about 932° F. to about 1202° F. (about 500° C. to about 650° C.) for a period of time ranging from about 0.5 hours to about 16 hours.

Another suitable method for preparing a dispersion of a base catalyst in a refractory inorganic oxide matrix component is to dry blend particles of each, preferably in finely divided form, and then to dimensionally form the dispersion if desired.

The dehydrogenation process of the present invention can begin with a hydrocarbon feedstock preheating step. The feedstock can be preheated in feed/reactor effluent heat exchangers prior to entering a furnace or contacting other high temperature waste heat means for final preheating to a targeted catalytic reaction zone inlet temperature. Suitable final preheating means can include, but are not limited to waste heat from other refinery processes such as a fluid catalytic cracking unit, a fluidized or delayed coking unit, a catalytic hydrocracker, a crude distillation unit, a catalytic reforming unit, and/or hydrotreating units found in conventional petroleum refineries.

The feedstock can be contacted with a hydrogen stream prior to, during, and/or after preheating, before the catalytic dehydrogenation reaction zone, in any one or more of the reactors in the reaction zone, or between reactors in a multiple reactor reaction zone. The process may also be operated in the substantial absence of supplemental hydrogen addition. A fundamental and invaluable aspect of the present invention is that the subject dehydrogenation catalyst can be effectively utilized without the addition of supplemental hydrogen in addition to that inherently released through the dehydrogenation reaction. The addition of supplemental hydrogen in the process can reduce the rate of catalyst deactivation, resulting in reduced catalyst regeneration requirements. However, hydrogen addition may also adversely affect olefin yield by directing the reaction stoichiometrically away from dehydrogenation and toward olefin saturation.

Where a supplemental hydrogen stream is added, the hydrogen stream can be pure hydrogen or can be in admixture with diluents such as low-boiling hydrocarbons, carbon monoxide, carbon dioxide, nitrogen, water, sulfur compounds, and the like. The hydrogen stream purity should be at least about 50% by volume hydrogen, preferably at least about 65% by volume hydrogen, and more preferably at least about 75% by volume hydrogen for best results. Hydrogen can be supplied from a hydrogen plant, a catalytic reforming facility, or other hydrogen-producing or hydrogen-recovery processes.

The reaction zone can include, but is not limited to, one or more fixed bed reactors containing the same or different catalysts, a moving column reactor and catalyst regeneration system, or a fluidized bed reactor and regenerator, with a fixed bed reactor process being preferred. The feedstock may be contacted with a catalyst or a catalyst bed in either upward, downward, or radial flow fashion with downflow being preferred. The reactants may be in the liquid phase, admixed liquid and vapor phase, or the vapor phase, with the best results obtained in the vapor phase.

Moving column reactors and regenerator systems such as that described in U.S. Pat. No. 3,647,680 to Greenwood et al. are known in the art and commonly used in processes such as catalytic reforming. The system generally comprises a vertical elongated reaction vessel comprising moving annular columns of catalyst wherein hydrocarbon is passed in out-to-in radial flow towards the center of the reaction vessel. Portions of the moving bed of catalyst are continuously directed to a regeneration system for regenerating the catalyst through combustion of coke components.

Fluidized bed reactors, which are commonly used in fluidized catalytic cracking and fluidized coking processes, fluidize the catalyst directly within the hydrocarbon feedstock, separate the catalyst from the reaction products, and direct the spent catalyst back to a regeneration zone for regeneration. The heat of reaction from the burning of coke from the catalyst generally supplies the heat requirements for sustaining the particular process reactions.

The preferred reaction zone facilities for use with the dehydrogenation process of the present invention are fixed bed reactors. It is preferred that the dehydrogenation reaction zone comprise at least two fixed bed reactors so as to facilitate on stream regeneration of the catalyst. The fixed bed reactors are generally equipped with proper manifolding to permit removal of each reactor from operation in a manner so as to provide for regeneration of the catalyst in that reactor while the other reactor or reactors sustain process operations. Fixed bed reactors in accordance with the present invention can also comprise a plurality of catalyst beds. The plurality of catalyst beds in a single fixed bed reactor can also comprise the same or different catalysts.

Since the dehydrogenation reaction is generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units such as from a fluid catalytic cracking process or a fluidized coker. Multiple reactor processes can provide reduced temperature endotherm per reactor shell and more effective temperature control but generally cost more in terms of capital requirements.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel. The hydrogen purge rate can be controlled to maintain minimum hydrogen purity. Recycled hydrogen can be compressed, supplemented with "make-up" hydrogen, and reinjected into the process for further dehydrogenation where supplemental hydrogen is added.

The stripper liquid effluent product is then generally conveyed to downstream processing facilities. The olefin product can be directed to an isomerization process for isomerization and thereafter directed to an ether facility for conversion, in the presence of alkanol, to an ether. Where at least a portion of the olefin from the process of the present invention is iso-olefin, the stream can be sent directly to an ether facility. Prior to direction to an ether facility, the product stream can be purified by removing unconverted paraffinic-hydrocarbon from the product. This unconverted product can be recycled back to the reaction zone or further manipulated in other process units. The olefin product can be directed to an alkylation process for reaction with isoparaffin to form higher octane, lower volatility gasoline blending components. The olefin product can be directed to a chemical manufacture process for conversion to other commodity chemical products or process streams. Methods for integration of the process of the present invention with other conventional refinery or chemical plant processes or products will be generally known to those skilled in the art.

Notwithstanding the superior stability properties of the dehydrogenation catalyst of the present invention, periodic catalyst regeneration may be required depending on the severity of operation and other process parameters. It is anticipated that the catalyst utilized in the process of the present invention may require regeneration as often as once every 6 months, as often as once every 3 months, and, on occasion, as often as once or twice every month. The dehydrogenation catalyst of the present invention is particularly suited for regeneration by the oxidation or burning of catalyst deactivating carbonaceous deposits with oxygen or an oxygen-containing gas. Moreover, catalyst performance is not generally diminished from periodic regeneration, in contradistinction to comparison catalysts tested. The term "regeneration," for purposes of the present invention, shall mean the recovery of at least a portion of the molecular sieve initial activity by combusting the coke deposits on the catalyst with oxygen or an oxygen-containing gas.

The prior art is replete with catalyst regeneration techniques that may be employed in the process of the present invention. Some of these regeneration techniques involve chemical methods for increasing the activity of deactivated molecular sieves. Others, including the preferred methods, relate to processes or methods for regenerating carbon (also known as coke) deactivated catalysts by the combustion of the coke with an oxygen-containing gas stream.

For example, U.S. Pat. No. 2,391,327 discloses the regeneration of catalysts contaminated with carbonaceous deposits with a cyclic flow of regeneration gases.

U.S. Pat. No. 3,755,961 relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieve.

U.S. Pat. No. 4,480,144 relates to the use of a circulating gas to regenerate a coke deactivated zeolite-containing catalyst. The circulating gas is maintained at a low moisture level by purging wet gases from the loop while simultaneously introducing dry gases into the loop. This method is particularly useful with zeolitic catalysts since zeolitic catalysts can be detrimentally effected by the presence of water.

The conditions and methods at which a catalyst may be regenerated by coke combustion can vary. It is typically desired to perform coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size, in the case of a continuous regeneration process.

Optimum regeneration conditions and methods are generally disclosed in the prior art as mentioned hereabove. Catalyst regeneration is typically accomplished at conditions including a temperature range of from about 550° F. to about 1300° F. (288° C. to about 704° C.), a pressure range of from about 0 psig to about 300 psig, and a regeneration gas oxygen content of from about 0.1 mole percent to about 23.0 mole percent. The oxygen content of the regeneration gas is typically increased during the course of a catalyst regeneration procedure based on catalyst bed outlet temperatures, in order to regenerate the catalyst as quickly as possible while avoiding catalyst-damaging process conditions.

The preferred catalyst regeneration conditions include a temperature ranging from about 600° F. to about 1150° F. (316° C. to about 621° C.), a pressure ranging from about 0 psig to about 150 psig, and a regeneration gas oxygen content of from about 0.1 mole percent to about 10 mole percent for best results.

Additionally, it is important that regeneration be accomplished in the presence of an oxygen-containing gas. The oxygen-containing regeneration gas typically comprises nitrogen and carbon combustion products such as carbon monoxide and carbon dioxide, to which oxygen in the form of air has been added. However, it is possible that the oxygen can be introduced into the regeneration gas as pure oxygen, or as a mixture of oxygen diluted with another gaseous component. Air is the preferred oxygen-containing gas.

Operating conditions to be used in the dehydrogenation process of the present invention include an average catalytic reaction zone temperature of from about 500° F. to about 1300° F. (260° C. to about 704° C.), preferably from about 700° F. to about 1200° F. (371° C. to about 649° C.), and more preferably from about 850° F. to about 1100° F. (454° C. to about 593° C.) for best results. Reaction temperatures below these ranges can result in reduced paraffin conversion and lower olefin yield. Reaction temperatures above these ranges can result in reduced olefin selectivity and lower olefin yields.

The process of the present invention generally operates at catalytic reaction zone pressures ranging from as low as substantially vacuum pressure (about 0 to about 27.6 inches of water vacuum) to about 500 psig, preferably from about vacuum pressure to about 300 psig, and more preferably from about vacuum pressure to about 1 00 psig for best results. Where the process operates in the presence of hydrogen, hydrogen circulation rates generally range from about 1 SCF/Bbl to about 12,000 SCF/Bbl, preferably from about 1 SCF/Bbl to about 6,000 SCF/Bbl, and most preferably from about 1 SCF/Bbl to about 1,000 SCF/Bbl for best results. Reaction pressures and hydrogen circulation rates below these ranges can result in higher catalyst deactivation rates resulting in increased energy intensive regeneration cycles. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield.

The process of the present invention generally operates at a weight hourly space velocity (WHSV) of from about 0.1 $hr^1$ to about 100 $hr^1$, preferably from about 0.5 $hr^1$ to about 40 $hr^1$, and most preferably from about 0.5 $hr^1$ to about 20 $hr^1$ for best results. Feed space velocities exceeding the levels described herein generally result in a decline in paraffin conversion which overwhelm any gain in olefin selectivity, thereby resulting in lower olefin yield. Feed space velocities short of the levels described herein are generally costly in terms of capital requirements.

The dehydrogenation catalyst and process of the present invention provides superior overall dehydrogenation properties closely approaching thermodynamic equilibrium. The dehydrogenation catalyst of the present invention can reach paraffin conversion levels in excess of 25 percent, typically in excess of 35 percent, and commonly in excess of 40 percent. Olefin selectivity levels are generally maintained in excess of 80 percent, typically in excess of 85 percent, and commonly exceed 90 percent. These levels of paraffin conversion and olefin selectivity result in olefin yield levels which generally exceed 25 percent, typically exceed 30 percent, and commonly exceed 35 percent.

The dehydrogenation catalyst and process of the present invention provides the above-described levels of performance while resisting catalyst deactivation, thereby extending catalyst cycle life under dehydrogenation conditions. The dehydrogenation catalyst of the present invention can and has achieved olefin yield deactivation loss levels of 0.4 percent conversion per day or less at a reaction temperature of about 1000° F. The catalyst of the present invention has maintained this level of resistance to deactivation over an on stream period in excess of 315 hours with only 1 regeneration. During this scenario, paraffin conversion and olefin selectivity surprisingly remained relatively constant, resulting in a relatively constant olefin yield.

The dehydrogenation catalyst and process of the present invention can be utilized for on stream periods in excess of 50 hours, 100 hours, 140 hours, and even in excess of one or more months at a reaction temperature of 1000° F. before requiring catalyst regeneration or replacement. As deactivation levels increase over time on stream, olefin selectivity may be reduced, thereby resulting in lower olefin yield and necessitating increased reaction temperatures. Increasing reaction temperatures to maintain olefin yield levels generally accelerate the deactivation process.

The dehydrogenation catalyst and process of the present invention are so effective with regard to catalyst stability and deactivation resistance that the catalyst can be operated in the absence of supplemental hydrogen addition. This is an extraordinary advantage of the process of the present invention for several reasons. Operating in the absence of supplemental hydrogen addition can avoid enormous capital and operating costs connected to the installation and operation of hydrogen recovery facilities which generally include hydrogen gas compressors and separation facilities such as high pressure process towers and membranes. Operating in the absence of supplemental hydrogen also favorably drives the dehydrogenation reaction stoichiometrically towards dehydrogenation and away from hydrogen saturation, in contradistinction to the prior art dehydrogenation processes which generally must be conducted in the presence of supplemental hydrogen addition in order to maintain a viable catalyst run length.

The dehydrogenation catalyst and process of the present invention can be retrofitted to utilize existing processes and facilities such as, but not limited to, those previously dedicated to naphtha reforming. The reaction pressure requirements are generally low and therefore, suitable reactor vessels may be located from any of several sources. A catalytic reformer may also possess furnace hardware, hydrocarbon separation, and catalyst regeneration equipment particularly synergistic to use with the process of the present invention. Catalytic reforming is also particularly suited for retrofit with the present invention in view of recent environmental mandates to produce gasolines containing lower aromatic concentrations (a fundamental product of catalytic reforming).

The present invention is described in further detail in connection with the following examples, it being understood that the same are for purposes of illustration and not limitation.

EXAMPLE 1

A paraffin dehydrogenation catalyst in accordance with the present invention and comprising about 54.18 percent by weight of an L zeolite molecular sieve, 36.12 percent by weight of a silica binder, 7.60 percent by weight of potassium, 1.80 percent by weight of zinc, and about 0.30 percent by weight of platinum was prepared for comparison with catalysts not in accordance with the present invention.

The dehydrogenation catalyst was prepared from a commercial potassium exchanged L zeolite molecular sieve component (ELZ-L) obtained from Union Carbide Corporation. The composition of the commercial potassium exchanged L zeolite molecular sieve expressed in terms of mole ratios was represented as follows:

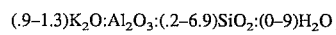

$(.9-1.3)K_2O:Al_2O_3:(.2-6.9)SiO_2:(0-9)H_2O$

L zeolite, its properties, and methods of preparation are described in U.S. Pat. No. 3,216,789, the disclosure of which has been incorporated by reference.

The dehydrogenation catalyst was prepared by incipient wetness impregnation of 57.9 grams of a potassium exchanged L zeolite molecular sieve with a solution containing 4.8 grams of zinc acetate ($Zn(OOCCH_3.2H_2O)$) and 36.0 grams of water. The zinc impregnated L zeolite molecular sieve was dried and calcined in air at 1000° F. for a period of 3 hours. The calcined particulate was impregnated using incipient wetness techniques with a solution containing 0.38 grams of platinum tetraamine nitrate ($Pt(NH_3)_4(NO_3)_2$) and 35.0 grams of distilled water. The platinum and zinc impregnated L zeolite molecular sieve was dried and 37.9 grams of the dried particulate mixed with 20.0 grams of CAB-O-SIL EH-5 silica (manufactured by Cabot Corporation) and 110.0 grams of distilled water in a small Waring blender for a period of 5 to 10 minutes. The mixture was dried at 250° F. for 16 hours in a forced air oven, crushed, and sized to 12 to 20 mesh (U.S. Sieve Series). The catalyst was designated as Catalyst 1.

EXAMPLE 2

A comparison paraffin dehydrogenation catalyst similar to Catalyst 1 but without zinc was prepared for comparison with the dehydrogenation catalyst in accordance with the present invention. The comparison catalyst comprised about 55.20 percent by weight of an L zeolite molecular sieve, 36.80 percent by weight of a silica binder, 7.70 percent by weight of potassium, and about 0.30 percent by weight of platinum.

The dehydrogenation catalyst was prepared by incipient wetness impregnation of 15.1 grams of a potassium exchanged L zeolite molecular sieve with a solution containing 0.15 grams of platinum tetraamine nitrate ($Pt(NH_3)_4(NO_3)_2$) and 14.0 grams of distilled water. The platinum impregnated L zeolite molecular sieve was dried and 15.0 grams of the dried particulate mixed with 10.0 grams of CAB-O-SIL EH-5 silica and 124.0 grams of distilled water in a small Waring blender for a period of 5 to 10 minutes. The mixture was dried at 250° F. for 16 hours in a forced air oven, crushed, and sized to 12 to 20 mesh (U.S. Sieve Series). The catalyst was designated as Catalyst 2.

EXAMPLE 3

A comparison paraffin dehydrogenation catalyst similar to Catalyst 1 but comprising a sodium-containing alumina support instead of a potassium exchanged L zeolite and silica-containing support was prepared for comparison with the dehydrogenation catalyst in accordance with the present invention. The comparison catalyst comprised about 95.90 percent by weight of an alumina support, 2.00 percent by weight of sodium, 1.80 percent by weight of zinc, and about 0.30 percent by weight of platinum.

The dehydrogenation catalyst was prepared by incipient wetness impregnation of 138.0 grams of Versal 450 Alumina, manufactured by LaRoche Chemicals, with a solution containing 10.1 grams of zinc acetate ($Zn(OOCCH_3.2H_2O)$) and 97.0 grams of water. The zinc impregnated alumina was dried and calcined in air at 1000° F. for a period of 3 hours. The calcined particulate (40.0 grams) was impregnated using incipient wetness techniques with a solution containing 0.40 grams of platinum tetraamine nitrate ($Pt(NH_3)_4(NO_3)_2$) and 40.0 grams of distilled water. The platinum and zinc impregnated alumina was dried and 40.0 grams of the dried particulate mixed with a solution containing 2.9 grams of sodium carbonate and 40.0 grams of distilled water. The zinc, platinum, and sodium impregnated alumina was dried and 30.0 grams of the particulate mixed with 15.0 grams of distilled water and compacted into 2 inch pellets. The pellets were dried, crushed, and sized to 12 to 20 mesh (U.S. Sieve Series). The catalyst was designated as Catalyst 3.

EXAMPLE 4

A paraffin dehydrogenation catalyst similar to Catalyst 1 but containing barium in place of the zinc was prepared for comparison with the dehydrogenation catalyst in accordance with the present invention. The comparison catalyst comprised about 68.47 percent by weight of an L zeolite molecular sieve, 17.12 percent by weight of a silica binder, 7.47 percent by weight of potassium, 5.65 percent by weight of barium, and about 1.29 percent by weight of platinum.

The dehydrogenation catalyst was prepared by first synthesizing a quantity of a barium and potassium exchanged L zeolite. This was accomplished by refluxing 200 grams of potassium exchanged L zeolite (as described in Example 1) with 100 grams of barium nitrate dissolved in 600 grams of deionized water. Refluxing was conducted at a temperature of 90° C. for a period of 3 hours. The barium and potassium exchanged L zeolite was filtered, dried, and reslurried with 600 grams of deionized water and refluxed for 1 hour. The washed barium and potassium exchanged L zeolite was filtered, dried at 120° C. for a period of 16 hours, and calcined at 500° C. for a period of 2 hours. The barium and potassium exchanged L zeolite was mixed with 50 grams of CAB-O-SIL EH-5 silica and 1000 grams of distilled water in a small homogenizer. The mixture was filtered, extruded into 1/16 inch extrudates, and dried at 120° C. for a period of 16 hours. The extruded barium and potassium exchanged L zeolite was then impregnated by incipient wetness techniques with 6.88 grams of platinum tetraamine nitrate ($Pt(NH_3)_4(NO_3)_2$) and 250.0 grams of distilled water. The platinum and barium and potassium exchanged L zeolite extrudates were dried at 120° C. for a period of 16 hours, crushed, and sized to 12 to 20 mesh (U.S. Sieve Series). The catalyst was designated as Catalyst 4.

EXAMPLE 5

A comparison paraffin dehydrogenation catalyst similar to that disclosed in U.S. Pat. No. 4,438,288 to Imai et al. (i.e. platinum, tin, and alkali or alkaline earth metals on an alumina support) was prepared for comparison with the dehydrogenation catalyst in accordance with the present invention. The comparison catalyst comprised about 96.80 percent by weight of an alumina support, 1.80 percent by weight of sodium, 1.20 percent by weight of tin, and about 0.30 percent by weight of platinum.

The dehydrogenation catalyst was prepared by incipient wetness impregnation of 70.0 grams of Versal 450 Alumina, manufactured by LaRoche Chemicals, with a solution containing 2.3 grams of tin (II) 2-ethylhexanoate ($Sn(OOCC_7H_{15})_2$) and 37.0 grams of n-hexane. The tin impregnated alumina was dried and calcined in air at 1000° F. for a period of 3 hours. The calcined particulate (51.4 grams) was impregnated using incipient wetness techniques with a solution containing 0.31 grams of platinum tetraamine nitrate ($Pt(NH_3)_4(NO_3)_2$) and 50.0 grams of distilled water. The platinum and tin impregnated alumina was dried and 50.0 grams of the dried particulate mixed with a solution containing 3.7 grams of sodium carbonate and 50.0 grams of distilled water. The tin, platinum, and sodium impregnated alumina was dried and 33.0 grams of the particulate mixed with 17.0 grams of distilled water and compacted into 2 inch pellets. The pellets were dried, crushed, and sized to 12 to 20 mesh (U.S. Sieve Series). The catalyst was designated as Catalyst 5.

EXAMPLE 6

A feedstock containing 99.5 weight percent isobutane was dehydrogenated over dehydrogenation Catalysts 1–5 from Examples 1–5. All catalysts were tested using a quartz bench-top reactor unit having a quartz tube reactor containing a packed bed. Operation was downflow with once-through hydrocarbon flow. Catalysts of 12 to 20 mesh size (U.S. Sieve Series) were used for testing and the catalysts were positioned between a top and bottom bed of 30 to 50 mesh size (U.S. Sieve Series) alpha alumina. All catalysts were activated by heating under a hydrogen flow from room temperature to 900° F. at a heating rate of 55° F./hour, held for 2 hours at 900° F., and then heated to 1000° F. under a nitrogen purge. The isobutane feedstock was processed through the quartz bench-top unit at varied experimental run lengths. All dehydrogenation reactions were conducted at a pressure of less than 1 psig. Gaseous products were analyzed on a Carle Refinery Gas Analyzer gas chromatograph.

The Catalyst testing conditions, product composition, and performance criteria in terms of isobutane conversion, isobutylene selectivity, and isobutylene yield (defined hereabove) were determined for ascending time on stream. The dehydrogenation results for Catalysts 1–5 are set forth in Tables 1–5.

Deactivation rates for Catalysts 1–5 in terms of conversion loss per day were calculated based on development of a regression line of the isobutylene yield data presented in Tables 1–5. The slope of the line was calculated from the regressed line for each of Catalysts 1–5 and is presented in Table 6 as the percent of initial conversion loss per day through deactivation.

TABLE 1

| Process Conditions | | | | | | | | | | | |
|---|---|---|---|---|---|---|---|---|---|---|---|
| Temperature, °F. | 1000 | 1000 | 1000 | 1000 | 1000 | 1000 | 1000 | 1000 | 1000 | 1000 | 1000 |
| Isobutane WHSV, hr$^{-1}$ | 2.7 | 2.8 | 2.9 | 3.0 | 2.9 | 2.9 | 2.9 | 2.9 | 2.9 | 2.9 | 2.9 |
| Time on Stream, hrs | 3.5 | 7.1 | 23.5 | 30.5 | 47.2 | 54.6 | 71.8 | 97.4 | 117.1 | 125.0 | 148.5 |
| Product Composition (mol) % | | | | | | | | | | | |
| Hydrogen | 28.36 | 28.47 | 28.76 | 28.28 | 28.64 | 28.32 | 28.70 | 28.48 | 28.34 | 27.80 | 27.53 |
| Methane | 0.26 | 0.25 | 0.22 | 0.20 | 0.20 | 0.19 | 0.19 | 0.19 | 0.17 | 0.18 | 0.18 |
| Ethane | 0.02 | 0.03 | 0.04 | 0.04 | 0.04 | 0.04 | 0.04 | 0.04 | 0.03 | 0.03 | 0.03 |
| Ethylene | 0.01 | 0.01 | 0.01 | 0.01 | 0.01 | 0.01 | 0.01 | 0.01 | 0.01 | 0.01 | 0.01 |
| Propane | 0.42 | 0.26 | 0.26 | 0.30 | 0.29 | 0.33 | 0.23 | 0.23 | 0.24 | 0.28 | 0.28 |
| Propylene | 0.48 | 0.12 | 0.11 | 0.17 | 0.17 | 0.27 | 0.10 | 0.10 | 0.12 | 0.29 | 0.30 |
| Butane | 0.69 | 0.42 | 0.39 | 0.39 | 0.38 | 0.51 | 0.39 | 0.42 | 0.40 | 0.42 | 0.42 |
| Isobutane | 42.25 | 42.76 | 42.55 | 42.95 | 42.84 | 42.61 | 43.15 | 43.28 | 43.69 | 44.09 | 44.52 |
| 2-butenes | 0.62 | 0.24 | 0.23 | 0.22 | 0.22 | 0.08 | 0.22 | 0.23 | 0.23 | 0.23 | 0.24 |
| 1,3-Butadiene | 0.00 | 0.00 | 0..00 | 0.00 | 0.00 | 0.00 | 0.00 | 0.00 | 0.00 | 0.00 | 0.00 |
| Isobutylene + 1-Butene | 26.89 | 27.44 | 27.43 | 27.44 | 27.21 | 27.64 | 26.98 | 27.02 | 26.77 | 26.67 | 26.49 |
| C5+ | 0.00 | 0.00 | 0.00 | 0.00 | 0.00 | 0.00 | 0.00 | 0.00 | 0.00 | 0.00 | 0.00 |
| Results | | | | | | | | | | | |
| Isobutane Conv. (%) | 41.03 | 40.22 | 40.27 | 40.11 | 39.97 | 40.65 | 39.48 | 39.49 | 39.03 | 38.93 | 38.56 |
| Isobutylene Sel. (%) | 91.48 | 95.38 | 95.61 | 95.38 | 95.41 | 95.08 | 95.84 | 95.68 | 95.71 | 94.86 | 94.78 |
| Isobutylene Yld. (%) | 37.53 | 38.36 | 38.50 | 38.26 | 38.13 | 38.56 | 37.84 | 37.78 | 37.36 | 36.93 | 36.55 |

TABLE 2

| Process Conditions | | | | | | |
|---|---|---|---|---|---|---|
| Temperature, °F. | 999 | 1001 | 1000 | 1000 | 1001 | 1001 |
| Isobutane WHSV, hr$^{-1}$ | 3.0 | 3.0 | 3.0 | 3.0 | 3.0 | 3.0 |
| Time on Stream, hrs | 0.2 | 1.0 | 2.0 | 3.2 | 6.1 | 6.6 |
| Product Composition (mol %) | | | | | | |
| Hydrogen | N/A* | 0.00 | 8.67 | 0.00 | 2.17 | 2.59 |
| Methane | 22.69 | 10.13 | 6.45 | 5.83 | 3.98 | 3.60 |
| Ethane | 0.46 | 0.44 | 0.37 | 0.42 | 0.29 | 0.27 |
| Ethylene | 0.47 | 0.39 | 0.31 | 0.32 | 0.33 | 0.32 |
| Propane | 0.18 | 0.17 | 0.15 | 0.19 | 0.15 | 0.14 |
| Propylene | 0.57 | 0.50 | 0.43 | 0.50 | 0.49 | 0.48 |

TABLE 2-continued

| | | | | | | |
|---|---|---|---|---|---|---|
| Butane | 0.06 | 0.07 | 0.08 | 0.10 | 0.09 | 0.09 |
| Isobutane | 58.65 | 76.41 | 74.21 | 83.02 | 83.58 | 83.82 |
| 2-Butenes | 0.19 | 0.17 | 0.15 | 0.18 | 0.16 | 0.16 |
| 1,1-Butadiene | 0.00 | 0.06 | 0.05 | 0.00 | 0.06 | 0.06 |
| Isobutylene + 1-Butene | 16.73 | 11.66 | 8.98 | 9.44 | 8.70 | 8.42 |
| C5+ | 0.00 | 0.00 | 0.15 | 0.00 | 0.00 | 0.05 |
| Results | | | | | | |
| Isobutane Conv. (%) | 41.35 | 23.59 | 18.75 | 16.98 | 14.56 | 13.95 |
| Isobutylene Sel. (%) | 40.46 | 49.43 | 52.45 | 55.59 | 61.06 | 61.96 |
| Isobutylene Yld. (%) | 16.73 | 11.66 | 9.83 | 9.44 | 8.89 | 8.64 |

*N/A - not analyzed

TABLE 3

| Process Conditions | | | | | | | |
|---|---|---|---|---|---|---|---|
| Temperature, °F. | 1000 | 1000 | 1000 | 1000 | 1000 | 1000 | 1000 |
| Isobutane WHSV, hr-$^1$ | 2.9 | 2.9 | 2.9 | 2.9 | 2.9 | 2.9 | 2.9 |
| Time on Stream, hrs | 4.1 | 6.5 | 23.2 | 30.8 | 47.4 | 53.4 | 71.0 |
| Product Composition (mol %) | | | | | | | |
| Hydrogen | 30.20 | 29.31 | 27.72 | 25.86 | 25.15 | 23.85 | 21.09 |
| Methane | 0.15 | 0.14 | 0.15 | 0.13 | 0.15 | 0.15 | 0.15 |
| Ethane | 0.01 | 0.01 | 0.01 | 0.01 | 0.01 | 0.37 | 0.29 |
| Ethylene | 0.00 | 0.01 | 0.01 | 0.01 | 0.01 | 0.02 | 0.01 |
| Propane | 0.23 | 0.24 | 0.16 | 0.20 | 0.17 | 0.27 | 0.21 |
| Propylene | 0.15 | 0.19 | 0.11 | 0.14 | 0.11 | 0.24 | 0.19 |
| Butane | 0.30 | 0.27 | 0.22 | 0.18 | 0.16 | 0.15 | 0.14 |
| Isobutane | 40.42 | 41.54 | 44.59 | 47.95 | 50.43 | 52.24 | 57.55 |
| 2-Butenes | 0.13 | 0.12 | 0.06 | 0.10 | 0.05 | 0.05 | 0.08 |
| 1,1-Butadiene | 0.01 | 0.00 | 0.00 | 0.00 | 0.00 | 0.00 | 0.00 |
| Isobutylene + 1-Butene | 28.40 | 28.17 | 26.97 | 25.42 | 23.76 | 22.68 | 20.29 |
| C5+ | 0.00 | 0.00 | 0.00 | 0.00 | 0.00 | 0.00 | 0.00 |
| Results | | | | | | | |
| Isobutane Conv. (%) | 42.09 | 41.24 | 38.31 | 35.32 | 32.62 | 31.41 | 27.07 |
| Isobutylene Sel. (%) | 96.67 | 96.62 | 97.41 | 97.07 | 97.30 | 94.83 | 94.97 |
| Isobutylene Yld. (%) | 40.68 | 39.85 | 37.32 | 34.29 | 31.74 | 29.78 | 25.71 |

TABLE 4

| Process Conditions | | | | | |
|---|---|---|---|---|---|
| Temperature, °F. | 1000 | 1000 | 1000 | 1000 | 1000 |
| Isobutane WHSV, hr-$^1$ | 7.8 | 7.8 | 7.8 | 7.8 | 7.8 |
| Time on Stream, hrs | 0.2 | 0.7 | 1.0 | 2.0 | 3.0 |
| Product Composition (mol %) | | | | | |
| Hydrogen | 5.74 | 4.49 | 4.35 | 4.29 | 3.88 |
| Methane | 17.25 | 12.30 | 11.07 | 7.86 | 7.19 |
| Ethane | 0.44 | 0.52 | 0.52 | 0.44 | 0.42 |
| Ethylene | 0.00 | 0.18 | 0.18 | 0.16 | 0.15 |
| Propane | 0.22 | 0.20 | 0.21 | 0.23 | 0.27 |
| Propylene | 0.30 | 0.15 | 0.17 | 0.30 | 0.31 |
| Butane | 0.07 | 0.09 | 0.12 | 0.11 | 0.11 |
| Isobutane | 61.95 | 72.28 | 74.00 | 78.67 | 80.07 |
| 2-Butenes | 0.12 | 0.14 | 0.17 | 0.14 | 0.15 |
| 1,1-Butadiene | 0.06 | 0.07 | 0.08 | 0.07 | 0.07 |
| Isobutylene + 1-Butene | 11.07 | 9.48 | 9.06 | 7.67 | 7.34 |
| C5+ | 2.78 | 0.10 | 0.07 | 0.06 | 0.04 |
| Results | | | | | |
| Isobutane Conv. (%) | 34.28 | 24.32 | 22.63 | 17.80 | 16.70 |
| Isobutylene Sel. (%) | 34.26 | 40.81 | 41.86 | 45.01 | 45.73 |
| Isobutylene Yld. (%) | 11.74 | 9.93 | 9.47 | 8.01 | 7.64 |

TABLE 5

| Process Conditions | | | | | | |
|---|---|---|---|---|---|---|
| Temperature, °F. | 1000 | 1001 | 1001 | 1001 | 1001 | 1002 |
| Isobutane WHSV, hr-[1] | 2.9 | 2.9 | 2..9 | 2.9 | 2.9 | 2.9 |
| Time on Stream, hrs | 4.0 | 5.6 | 21.8 | 29.5 | 45.8 | 52.8 |
| Product Composition (mol %) | | | | | | |
| Hydrogen | 28.17 | 27.48 | 23.69 | 23.29 | 19.93 | 19.36 |
| Methane | 0.13 | 0.12 | 0.09 | 0.09 | 0.09 | 0.10 |
| Ethane | 0.01 | 0.01 | 0.00 | 0.00 | 0.00 | 0.00 |
| Ethylene | 0.01 | 0.00 | 0.00 | 0.00 | 0.00 | 0.00 |
| Propane | 0.24 | 0.22 | 0.24 | 0.25 | 0.18 | 0.19 |
| Propylene | 0.17 | 0.15 | 0.35 | 0.37 | 0.13 | 0.15 |
| Butane | 0.22 | 0.19 | 0.27 | 0.25 | 0.12 | 0.12 |
| Isobutane | 43.23 | 44.14 | 51.27 | 53.30 | 59.38 | 61.02 |
| 2-Butenes | 0.14 | 0.13 | 0.12 | 0.03 | 0.03 | 0.02 |
| 1,1-Butadiene | 0.00 | 0.00 | 0.00 | 0.00 | 0.00 | 0.00 |
| Isobutylene + 1-Butene | 27.68 | 27.56 | 23.97 | 22.44 | 20.14 | 19.04 |
| C5+ | 0.00 | 0.00 | 0.00 | 0.00 | 0.00 | 0.00 |
| Results | | | | | | |
| Isobutane Conv. (%) | 39.82 | 39.13 | 32.81 | 30.52 | 25.84 | 24.33 |
| Isobutylene Sel. (%) | 96.78 | 97.11 | 95.73 | 95.86 | 97.34 | 97.04 |
| Isobutylene Yld. (%) | 38.54 | 38.00 | 31.41 | 29.26 | 25.15 | 23.61 |

Catalyst 1, in accordance with the present invention and comprising platinum and zinc on a support comprising potassium exchanged L zeolite and silica, provided superior isobutane conversion (40%), isobutylene selectivity (95+), and isobutylene yields (38%) at a reaction temperature of about 1000° F. Over a period of 148.5 hours on stream, isobutane conversion was reduced slightly while isobutylene selectivity remained relatively constant, resulting in an isobutylene yield reduction of about 0.4 percent conversion loss per day.

Catalyst 2, a comparison catalyst comprising platinum on a support comprising potassium exchanged L zeolite and silica and absent the zinc of Catalyst 1, provided similar initial isobutane conversion (41%) but substantially lower isobutylene selectivity (40%) than Catalyst 1, resulting in a substantially lower isobutylene yield of 17%. Moreover, isobutane yield dropped off precipitously, overwhelming increases to isobutylene selectivity, and resulting in an isobutylene yield of less than 9% within a period of only 6 hours on stream. The isobutylene yield deactivation rate for Catalyst 2, extrapolated to a full days run length, was 101.8 percent conversion loss per day.

Catalyst 3, a comparison catalyst comprising platinum and zinc on a support comprising sodium and alumina (in place of the potassium exchanged L zeolite support of Catalyst 1), provided slightly higher initial isobutane conversion (42%), isobutylene selectivity (97%), and isobutylene yield (40%) than Catalyst 1 for a period of only 6.5 hours. Thereafter, isobutane conversion dropped off precipitously, resulting in an isobutylene deactivation rate of about 5.4 percent conversion loss per day. This isobutylene yield deactivation rate far exceeds the deactivation rate of Catalyst 1 in accordance with the present invention.

Catalyst 4, a comparison catalyst comprising platinum and barium (in place of the zinc of Catalyst 1) on a support comprising potassium exchanged L zeolite, provided poor initial and subsequent isobutane conversion (34%), isobutylene selectivity (34%), and isobutylene yield (12%). While the isobutylene selectivity improved slightly over the 3 hours on stream, the isobutane conversion loss rate far exceeded the rate of increase in isobutylene selectivity to where isobutylene yield was less than 8 percent. The isobutylene yield deactivation rate for Catalyst 4, extrapolated to a full days run length, was 148.9 percent conversion loss per day.

Catalyst 5, a comparison catalyst comprising platinum and tin (substituted for the zinc of Catalyst 1) on a support comprising alumina (in place of the potassium exchanged L zeolite support of Catalyst 1), provided good initial isobutane conversion (39%), isobutylene selectivity (97%), and isobutylene yield (38%) for a period of only 5.6 hours. Thereafter, isobutane conversion dropped off precipitously, resulting in an isobutylene yield deactivation rate of about 7.6 percent conversion loss per day. This deactivation rate far exceeds the deactivation rate of Catalyst 1 in accordance with the present invention.

TABLE 6

| Catalyst | Temperature, °F. | WHSV, hr-[1] | Deactivation, % Conversion/Day |
|---|---|---|---|
| Catalyst 1 | 1000 | 2.9 | 0.4 |
| Catalyst 2 | 1000 | 3.0 | 101.8 |
| Catalyst 3 | 1000 | 2.9 | 5.4 |
| Catalyst 4 | 1000 | 7.8 | 148.9 |
| Catalyst 5 | 1000 | 2.9 | 7.6 |

EXAMPLE 7

A dehydrogenation catalyst in accordance with the present invention was regenerated for evaluation of catalyst performance after exposure of the catalyst to regeneration conditions. After dehydrogenating isobutane with Catalyst 1 for a period of 148.5 hours under the conditions set forth in Example 6, a portion of Catalyst 1 was regenerated ex-situ by placing it in an oven at 750° F. under a 0.5% oxygen/99.5% nitrogen atmosphere for a period of about 72 hours. The regenerated catalyst was designated as Catalyst 6. Isobutane was dehydrogenated over Catalyst 6 in a manner similar to that described in Example 6 for an additional 169.1 hours. The dehydrogenation results are set forth in Table 7.

TABLE 7

| Process Conditions | | | | | | |
|---|---|---|---|---|---|---|
| Temperature, °F. | 999 | 1001 | 1001 | 1002 | 1003 | 1001 |
| Isobutane WHSV, hr$^{-1}$ | 3.2 | 3.2 | 3.2 | 3.2 | 3.2 | 3.2 |
| Time on Stream, hrs | 150.4 | 166.7 | 191.2 | 215.6 | 239.6 | 317.6 |
| Product Composition (mol %) | | | | | | |
| Hydrogen | 30.15 | 28.46 | 28.56 | 27.87 | 27.74 | 27.65 |
| Methane | 0.40 | 0.17 | 0.15 | 0.16 | 0.14 | 0.13 |
| Ethane | 0.10 | 0.03 | 0.03 | 0.03 | 0.03 | 0.03 |
| Ethylene | 0.00 | 0.00 | 0.00 | 0.00 | 0.00 | 0.00 |
| Propane | 0.46 | 0.30 | 0.25 | 0.20 | 0.19 | 0.13 |
| Propylene | 0.14 | 0.12 | 0.11 | 0.21 | 0.22 | 0.21 |
| Butane | 1.00 | 0.39 | 0.33 | 0.43 | 0.44 | 0.46 |
| Isobutane | 39.15 | 43.08 | 43.01 | 43.85 | 44.19 | 44.60 |
| 2-Butenes | 0.59 | 0.24 | 0.18 | 0.27 | 0.28 | 0.34 |
| 1,1-Butadiene | 0.00 | 0.01 | 0.01 | 0.04 | 0.04 | 0.04 |
| Isobutylene + 1-Butene | 28.01 | 27.21 | 27.37 | 26.95 | 26.73 | 26.41 |
| C5+ | 0.00 | 0.00 | 0.00 | 0.00 | 0.00 | 0.00 |
| Results | | | | | | |
| Isobutane Conv. (%) | 43.96 | 39.78 | 39.80 | 39.21 | 38.85 | 38.36 |
| Isobutylene Sel. (%) | 91.25 | 95.61 | 96.27 | 95.30 | 95.23 | 95.17 |
| Isobutylene Yld. (%) | 40.10 | 38.03 | 38.31 | 37.36 | 36.99 | 36.50 |

Example 7 and Catalyst 6 illustrate that the dehydrogenation catalyst in accordance with the present invention can catalyze dehydrogenation for a period of in excess of 315 hours on stream while still maintaining superior yields of isobutylene. Additionally, Catalyst 6 illustrates that a catalyst in accordance with the present invention can undergo a regeneration sequence while maintaining superior performance.

Over the incremental 169.1 hours of operation after regeneration, dehydrogenation performance closely mirrored the dehydrogenation performance of the fresh Catalyst 1 during initial dehydrogenation described in Example 6. After 169.1 hours on stream and after regeneration, isobutane conversion, isobutylene selectivity, and isobutylene yield were very close to that of fresh Catalyst 1 after 148.5 hours on stream. Therefore, the catalyst in accordance with the present invention provides extraordinary stability advantages compared to the catalysts of the prior art that permit it to be regenerated over and over while still maintaining superior olefin yields.

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. A process for dehydrogenating a hydrocarbon feedstock and producing an olefinic product comprising contacting said feedstock at dehydrogenation conditions with a dehydrogenation catalyst, said dehydrogenation catalyst comprising from about 0.01 weight percent to about 5.0 weight percent of a platinum group metal, from about 0.02 weight percent to about 10.0 weight percent of zinc, and a support component comprising an L zeolite molecular sieve and an alkali metal.

2. The process of claim 1 wherein said platinum group metal comprises platinum.

3. The process of claim 1 wherein said alkali metal comprises potassium.

4. The process of claim 1 wherein said dehydrogenation catalyst comprises an L zeolite molecular sieve in an amount ranging from about 20 weight percent to about 80 weight percent.

5. The process of claim 1 wherein said support component further comprises an inorganic oxide matrix comprising silica.

6. The process of claim 1 wherein said hydrocarbon feedstock comprises paraffinic hydrocarbon having from 2 to 20 carbon atoms and at least a portion of said feedstock is in the vapor phase at said dehydrogenation conditions.

7. The process of claim 1 wherein said dehydrogenation conditions comprise a reaction temperature of from about 500° F. to about 1500° F., a reaction pressure of from about vacuum to about 500 psig, and a WHSV of from about 0.1 to about 100.0.

8. A process for dehydrogenating a paraffinic hydrocarbon feedstock and producing an olefinic product comprising contacting said feedstock at dehydrogenation conditions with a dehydrogenation catalyst, said dehydrogenation catalyst comprising from about 0.10 weight percent to about 3.0 weight percent of platinum, from about 0.02 weight percent to about 10.0 weight percent of zinc, from about 20.0 weight percent to about 80.0 weight percent of an L zeolite molecular sieve, and from about 0.10 weight percent to about 10.0 weight percent of potassium.

9. The process of claim 8 wherein said dehydrogenation catalyst further comprises an inorganic oxide matrix comprising silica.

10. The process of claim 8 wherein said hydrocarbon feedstock comprises paraffinic hydrocarbon having from 2 to 12 carbon atoms and at least a portion of said feedstock is in the vapor phase at said dehydrogenation conditions.

11. The process of claim 8 wherein said dehydrogenation conditions comprise a reaction temperature of from about 700° F. to about 1200° F., a reaction pressure of from about vacuum to about 300 psig, and a WHSV of from about 0.5 to about 40.0.

12. The process of claim 8 wherein said dehydrogenation catalyst comprises from about 0.10 weight percent to about 2.0 weight percent of platinum, from about 0.20 weight percent to about 5.0 weight percent of zinc, from about 40.0 weight percent to about 60.0 weight percent of an L zeolite molecular sieve, from about 0.5 weight percent to about 8.0 weight percent potassium, and from about 40.0 to about 60.0 weight percent of silica.

13. The process of claim 8 wherein said contacting step is conducted in the substantial absence of supplemental hydrogen addition.

* * * * *

UNITED STATES PATENT AND TRADEMARK OFFICE
CERTIFICATE OF CORRECTION

PATENT NO.: 5,453,558

DATED: September 26, 1995

INVENTOR(S): Bruce D. Alexander, George A. Huff, Jr.

It is certified that error appears in the above-identified patent and that said Letters Patent is hereby corrected as shown below:

| Col. | Line | |
|---|---|---|
| 5 | 58 | "$(.9-1.1)M_{2/n}O:Al_2O_3:(.2-6.9)SiO_2:yH_2O$" should read --$(.9-1.1)M_{2/n}O:Al_2O_3:(5.2-6.9)SiO_2:yH_2O$-- |
| 6 | 65 | "$(.9-1.3)[(1-x)K_2O,xNa_2O]:Al_2O_3:(.2-6.9)SiO_2:yH_2O$" should read --$(.9-1.3)[(1-x)K_2O,xNa_2O]:Al_2O_3:(5.2-6.9)SiO_2:yH_2O$-- |
| 16 | 67 | "$(.9-1.3)K_2O:Al_2O_3:(.2-6.9)SiO_2:(0-9)H_2O$" should read --$(.9-1.3)K_2O:Al_2O_3:(5.2-6.9)SiO_2:(0-9)H_2O$-- |
| 21 | 5 | in "TABLE 2-continued" in the column labeled "Process Conditions" patent reads "1,1-Butadiene" patent should read -- 1,3-Butadiene -- |

UNITED STATES PATENT AND TRADEMARK OFFICE
CERTIFICATE OF CORRECTION

PATENT NO.: 5,453,558

DATED: September 26, 1995

INVENTOR(S): Bruce D. Alexander, George A. Huff, Jr.

It is certified that error appears in the above-identified patent and that said Letters Patent is hereby corrected as shown below:

| Col. | Line | |
|---|---|---|
| 21 | 30 | in "TABLE 3" in the column labeled "Process Conditions" patent reads "1,1-Butadiene" patent should read  -- 1,3-Butadiene -- |
| 21 | 54 | in "TABLE 4" in the column labeled "Process Conditions" patent reads "1,1-Butadiene" patent should read  -- 1,3-Butadiene -- |
| 23 | 15 | in "TABLE 5" in the column labeled "Process Conditions" patent reads "1,1-Butadiene" patent should read  -- 1,3-Butadiene -- |
| 23 | 29-30 | "isobutylene selectivity ($95^+$ )," should read  --isobutylene selectivity ($95^+$ %),--. |

UNITED STATES PATENT AND TRADEMARK OFFICE
CERTIFICATE OF CORRECTION

PATENT NO.: 5,453,558

DATED: September 26, 1995

INVENTOR(S): Bruce D. Alexander, George A. Huff, Jr.

It is certified that error appears in the above-identified patent and that said Letters Patent is hereby corrected as shown below:

| Col. | Line | |
|---|---|---|
| 25 | 10 | in "TABLE 7" in the fifth column from the left margin and in the row beginning with "Methane" patent reads<br>"0.40   0.17   0.15   0.16   0.14   0.13"<br>patent should read<br>--0.40   0.17   0.15   0.15   0.14   0.13-- |
| 25 | 17 | in "TABLE 7" in the column labeled "Process Conditions" patent reads "1,1-Butadiene" patent should read   -- 1,3-Butadiene -- |

UNITED STATES PATENT AND TRADEMARK OFFICE
CERTIFICATE OF CORRECTION

PATENT NO. : 5,453,558

DATED : September 26, 1995

INVENTOR(S) : Bruce D. Alexander, George A. Huff, Jr.

It is certified that error appears in the above-indentified patent and that said Letters Patent is hereby corrected as shown below:

```
25   20   in "TABLE 7" in the second column from the left
          margin and in the row beginning with "Isobutane
          Conv. (%)"  patent reads
          "43.96   39.78   39.80   39.21   38.85   38.36"
          patent should read
          --43.95   39.78   39.80   39.21   38.85   38.36--
```

Signed and Sealed this

Seventh Day of May, 1996

Attest:

BRUCE LEHMAN

Attesting Officer

Commissioner of Patents and Trademarks